United States Patent [19]

Gyulay

[11] Patent Number: 4,647,428

[45] Date of Patent: * Mar. 3, 1987

[54] AIR FRESHENER METHOD

[76] Inventor: Joseph M. Gyulay, Box 81361, Cleveland, Ohio 44181

[*] Notice: The portion of the term of this patent subsequent to Apr. 1, 2003 has been disclaimed.

[21] Appl. No.: 845,456

[22] Filed: Mar. 28, 1986

Related U.S. Application Data

[63] Continuation of Ser. No. 616,689, Jun. 4, 1984, Pat. No. 4,579,717.

[51] Int. Cl.⁴ .......................... A61L 9/02; A61L 9/03
[52] U.S. Cl. ...................................... 422/4; 422/125; 422/305; 422/306
[58] Field of Search ................... 422/4, 120, 121, 122, 422/123, 124, 125, 126, 305, 306

[56] References Cited

U.S. PATENT DOCUMENTS

| | | | |
|---|---|---|---|
| 1,403,548 | 1/1922 | Gudeman | 422/125 |
| 1,535,287 | 4/1925 | Beeler . | |
| 1,535,486 | 4/1925 | Lundy | 422/125 X |
| 1,556,680 | 10/1925 | Dorment | 422/125 |
| 1,565,500 | 12/1925 | Ritter . | |
| 1,732,707 | 10/1929 | Winsboro | 422/125 |
| 1,864,980 | 6/1932 | Curran | 422/125 X |
| 1,920,599 | 8/1933 | Schuh | 422/125 X |
| 1,966,738 | 7/1934 | Seewagon | 422/125 |
| 2,124,543 | 7/1938 | Clyne | 422/305 X |
| 2,143,246 | 1/1939 | McGary . | |
| 2,207,889 | 7/1940 | Kingman | 422/125 X |
| 2,238,476 | 4/1941 | Monteith | 422/125 X |
| 2,372,371 | 3/1945 | Eisner . | |
| 2,435,756 | 2/1948 | Schlesinger | 422/125 X |
| 2,468,164 | 4/1949 | Brewster | 422/125 X |
| 2,535,802 | 12/1950 | Libson | 422/125 |
| 2,539,696 | 1/1951 | Morrison | 422/125 |
| 2,557,501 | 6/1951 | Pusay et al. . | |
| 2,588,471 | 3/1952 | Bauer | 422/125 |
| 2,694,771 | 11/1954 | Cox | 422/125 X |
| 2,741,812 | 4/1956 | Tellier | 422/125 X |
| 3,763,347 | 10/1973 | Whitaker | 422/125 X |
| 3,930,796 | 1/1976 | Haensel | 422/180 X |
| 4,074,111 | 2/1978 | Hunter | 422/125 X |
| 4,579,717 | 4/1986 | Gyulay | 422/125 |

Primary Examiner—Barry S. Richman
Assistant Examiner—Jill Johnston
Attorney, Agent, or Firm—Bell, Seltzer, Park & Gibson

[57] ABSTRACT

A room air freshener in the form of a porous ceramic ring in combination with an uprightly positioned light bulb. The ring includes a liquid premeasuring cavity so that a fragrance-generating liquid filling the cavity will be completely absorbed by the ceramic ring. When the liquid filling the cavity is entirely absorbed by the ring, the ring may be placed on a light bulb for vaporization of the absorbed liquid and without risk of spillage regardless of the attitude or levelness of the ring on the bulb. When the lamp bulb is turned on, the ring is heated to vaporize the liquid and release the fragrance which permeates the room.

2 Claims, 8 Drawing Figures

U.S. Patent   Mar. 3, 1987   4,647,428
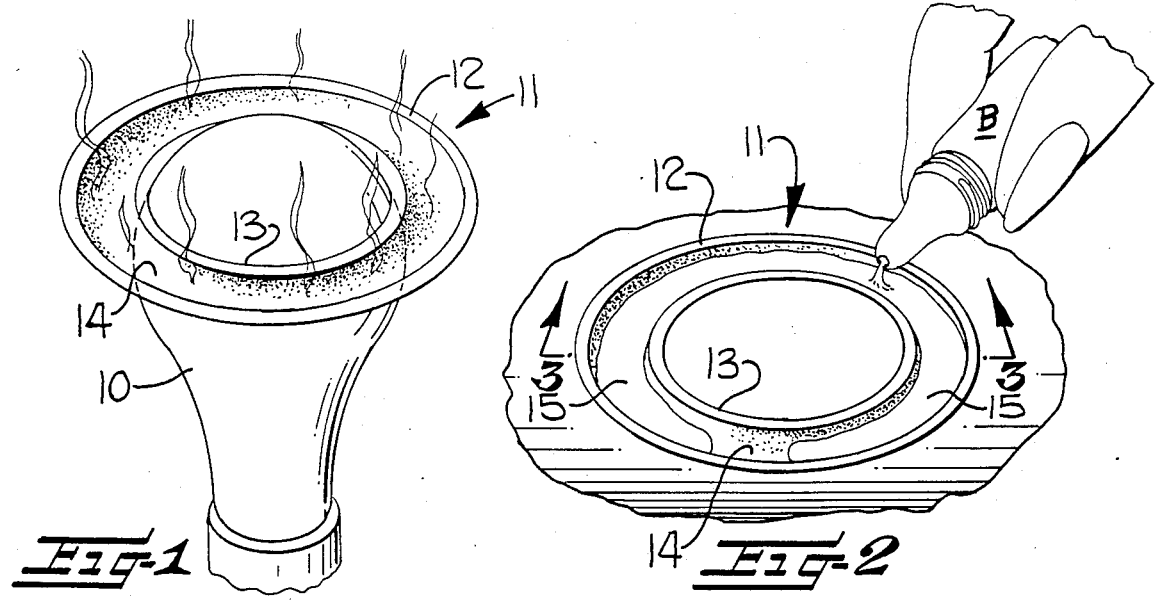
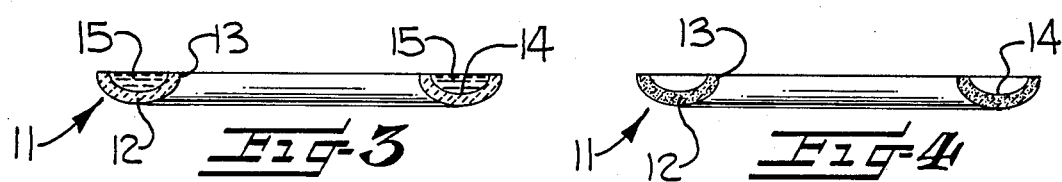
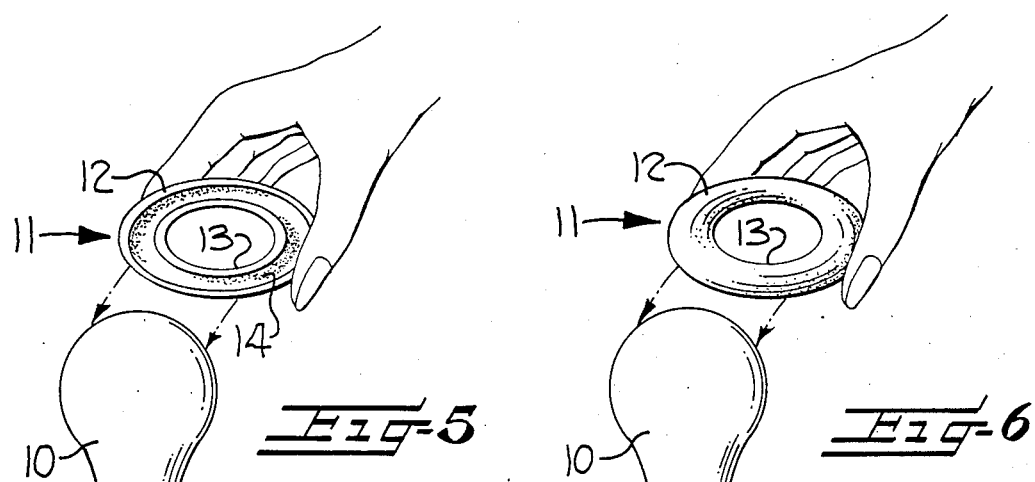
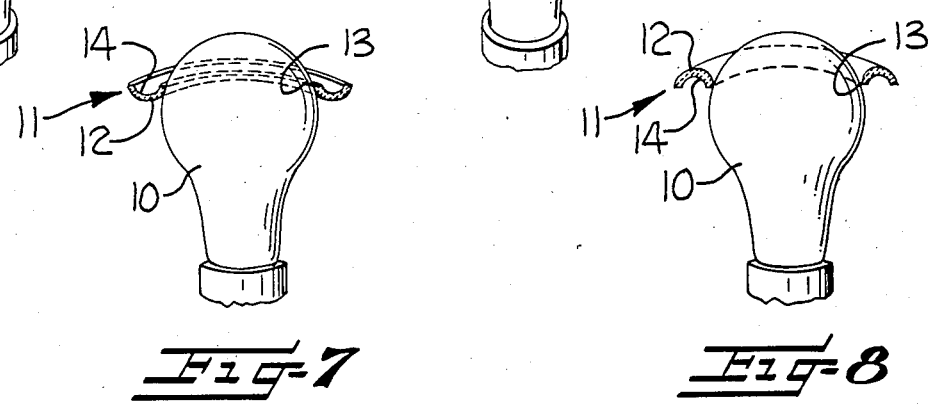

AIR FRESHENER METHOD

This application is a continuation of co-pending application Ser. No. 616,689; filed June 4, 1984 and entitled "Air Freshener", now U.S. Pat. No. 4,579,717.

BACKGROUND OF THE INVENTION

The present invention relates to the freshening or fragrancing of the air in an enclosed area by using devices and methods for distributing such a fragrance or freshener.

A number of devices and methods for air freshening or fragrancing have been available for some time. Common devices include aerosol sprays, scented candles, impregnated waxes and various electrical and mechanical devices which draw a fragrance out of a storage device of some sort and then distribute it throughout a room.

Although advantageous in some respects, many of these devices are unsuitable for certain applications. Aerosol sprays require active distribution by a user in periodic fashion while candles use open flames which must be carefully attended. The newer mechanical-electrical gadgets are quite interesting, but many are relatively expensive and are most suitable to professional applications or for those willing to indulge in expensive gadgetry.

More specific attemps have focused on the use of containers placed adjacent to light bulbs so that the heat from the bulb encourages a liquid or solid fragrant material in the container to evaporate and scent a room. The disadvantage of most of these devices is that the liquid fragrant material must be carefully added while the container is adjacent the bulb. Alternatively, if the container is filled with liquid away from the bulb, the filled container must be carefully transferred to and positioned on the bulb in order to avoid spilling the contents. Other such devices must be "loaded" by literally soaking them in fragrant materials and more than a few of the devices are relatively complicated in view of the rather straightforward effect desired.

Accordingly, it is an object of this invention to provide relatively inexpensive room air freshener which operates safely while unattended, which can take advantage of the otherwise wasted heat energy generated by a light bulb, which can be easily filled with fragrant material and which can be positioned adjacent a light bulb.

SUMMARY OF THE INVENTION

The present invention comprises a method and apparatus for imparting a desired fragrance to an area surrounding an uprightly positioned light bulb. The apparatus comprises the combination of an air freshener device with an uprightly positioned light bulb in an electric lamp. The device comprises an annular ring having a porous ceramic body. The internal opening of the ring receives upper portions of the light bulb in supporting and heat-receiving relation. For ease of operation, the ring body has a liquid premeasuring cavity of a predetermined volume less than the combined volume of the pores of the ceramic ring. When filled with a fragrant oil the cavity holds an amount which will be completely absorbed within the surrounding porous ceramic body prior to the ring being placed on a heated light bulb. The ceramic material from which the body is formed is capable of absorbing a oil therein to leave a dry outer surface. The insulating properties of the ceramic material likewise maintain the body at a relatively low temperature compared to the outer surface of the lamp when the bulb is energized and with which the ring is in contact. Once the ring is on the bulb, the absorbed oil is vaporized to fragrance or freshen the room air. The ring's capability for premeasuring and absorbing the oil allows the ring to be placed on the light bulb without risk of spillage regardless of the attitude or levelness of the ring on the bulb or of any handling operations in between. The overall size of the ring is such that the ring does not interfere appreciably with light transmission from the bulb.

DESCRIPTION OF THE DRAWINGS

The foregoing and other objects, advantages and features of the invention, and the manner in which the same are accomplished will become more readily apparent upon consideration of the following detailed description of the invention taken in conjunction with the accompanying drawings, which illustrate preferred and exemplary embodiments and wherein:

FIG. 1 is a perspective view of the invention showing the device received on a light bulb;

FIG. 2 is a perspective view of the device being filled with a fragrance-generating liquid;

FIG. 3 is a cross sectional view of the device taken along lines 3—3 of FIG. 2 and showing a fragrant oil filling the cavity of the ring;

FIG. 4 is another cross sectional view similar to FIG. 3, but after the fragrant oil has been absorbed into the ring;

FIG. 5 is a perspective view showing the device being placed upon a light bulb;

FIG. 6 is a view similar to FIG. 5 except that the orientation of the ring with respect to the light bulb has been reversed, i.e. the ring is upside down;

FIG. 7 is a partial sectional view of the device supportingly positioned on a light bulb; and FIG. 8 is a partial sectional view of the device received upside down on a light bulb.

DETAILED DESCRIPTION

As best illustrated in FIG. 1, the invention comprises an uprightly positioned light bulb 10 and an air freshener device in the shape of an annular ring broadly designated at 11. The ring 11 has a porous ceramic body 12 and contains an internal opening 13, so that the ring 11 is supported in heat receiving relation by and on the light bulb 10. It will be understood that the exact geometry of the device can be other than a perfect circle and that other polygonal shapes can depart from a circle while otherwise mimicking the structure and functions of the ring 11, the ceramic body 12 and the internal opening 13. Similarly, the inner surface of the ring 11 might have feet for making supporting engagement with the lamp bulb.

The ceramic body 12 has a liquid premeasuring cavity 14 of a predetermined volume. As shown, the cavity 14 is positioned inwardly from and surrounds the internal opening 13 of the ring 11. The volume of the premeasuring cavity 14 is such that when a liquid fills the cavity, as illustrated in FIG. 2 in which a fragrant oil is shown as being added from a bottle B, the cavity 14 holds an amount of oil which will be completely absorbed within the surrounding porous ceramic body 12. In this manner, a volume of fragrant oil 15 which fills the cavity 14 will be entirely absorbed by the porous ceramic body before the body is placed on the light bulb 10. Because of this relationship between the volume of the cavity 14 and the porous ceramic body 12 of the ring 11, the ring may be placed in heat transfer and fragrance-generating relation on the light bulb 10 without risk of spillage regardless of the attitude or levelness of the ring on the bulb, or of any handling steps in between.

The fragrant oil used generates a fragrance either with or without exposure to heat.

In this regard, FIG. 3 illustrates the ring 11 after sufficient fragrant oil has been added to fill the cavity 14. After a relatively short period of time, the porous ceramic body 12 absorbs all of the oil 15 in the cavity 14 and the ring 11 has a dry outer surface and the appearance of being empty of liquid as illustrated in FIG. 4.

With the oil so absorbed, the ring 12 may be placed in supporting and heat receiving relation on the light bulb 10 in a number of orientations, including those illustrated in FIGS. 5 and 6 respectively in which the ring 12 is illustrated as right side up and upside down. In like manner, FIGS. 7 and 8 show partial cross sectional views of the ring when supportingly positioned on the light bulb.

Because the ceramic material from which the ring is formed is an insulator, an energized light bulb heats the ring to a temperature which is relatively low compared to the outer surface of the bulb, but sufficient to vaporize the fragrant oil absorbed therein. Similarly, the overall size of the ring does not interfere appreciably with light transmission from the bulb. Alternatively, the ring can be left in place for long periods of time with the lamp bulb off when no fragrance emission is desired.

Accordingly, the invention also comprises a method of imparting a desired fragrance to an area surrounding an uprightly positioned light bulb. The method comprises providing the ring 11 with the porous ceramic body 12 and the liquid receiving cavity 14 therein for holding a predetermined volume of oil of such a measurement that a volume of oil which fills the cavity 14 will be completely absorbed within the porous ceramic body 12. As stated above, the opening 13 of the ring 11 is of sufficient size to receive upper portions of the light bulb so as not to be readily dislodged therefrom. As illustrated in FIG. 2, the method includes pouring a fragrance-generating liquid 15 into the cavity 14 in the ring to thereby obtain a predetermined volume of oil in the cavity when the cavity is filled with oil. This is best illustrated in FIG. 3.

As illustrated in FIG. 4, the cavity 14 is drained and spillage avoided by allowing the oil 15 in the cavity 14 to be absorbed into and throughout the porous ceramic body 12. Thereafter, the ring 11 with the oil absorbed therein is placed upon upper portions of the light bulb 10 for being removably supported thereon. In such a position, when the light bulb is energized, the absorbed fragrant oil in the porous ceramic body 12 of the ring 11 will be vaporized due to the heat applied thereto by the light bulb.

As a further feature of the invention, the method can include removing the ring 12 from the light bulb 10 upon vaporization of the absorbed oil originally placed therein. Fragrant oil can then be again added into the cavity 14 to gain obtain a predetermined volume of oil in the cavity when the cavity is filled. The cavity can again be drained while avoiding spillage by allowing the oil in the cavity to be absorbed into and throughout the porous ring. Thereafter, the ring 11 can be replaced on upper portions of the light bulb 10 whereby the heat generated by the light bulb again will vaporize the absorbed liquid in the porous ceramic body 12.

The foregoing embodiments are to be considered illustrative rather than restrictive of the invention, and those modifications which come within the meaning and range of equivalence of the claims are to be included therein.

That which is claimed is:

1. A method of imparting a desired fragrance to an area surrounding an uprightly positioned light bulb, without interfering appreciably with light transmission from the bulb, said method comprising:
   (a) providing a porous ceramic ring having a oil receiving cavity therein for holding a predetermined volume of oil, the pores of the porous ceramic ring having a combined volume sufficiently greater than the volume of the oil receiving cavity so that a volume of oil which fills the oil receiving cavity will be completely absorbed within the porous ceramic ring and wherein the inner circumference of the porous ceramic ring is of sufficient size to receive upper portions of a light bulb so as not to be readily dislodged therefrom;
   (b) pouring a fragrant oil into the oil receiving cavity in the porous ceramic ring to thereby obtain a predetermined volume of fragrant oil in the oil receiving cavity when the oil receiving cavity is filled with the fragrant oil;
   (c) draining the oil receiving cavity and avoiding spillage by allowing the fragrant oil in the oil receiving cavity to be completely absorbed into and throughout the porous ceramic ring so as to provide a dry oil receiving cavity and a dry outer surface of the porous ceramic ring; and
   (d) thereafter placing the porous ceramic ring with the fragrant oil absorbed therein upon upper portions of a light bulb so as to be removably supported thereon, and so as to be heated to a temperature which is relatively low compared to the outer surface of the light bulb when the light bulb is energized, but which is sufficient so that upon the light bulb being energized the absorbed fragrance-generating liquid in the porous ceramic ring will be vaporized due to the heat applied thereto by the light bulb.

2. A method according to claim 1 further comprising removing the porous ceramic ring from the light bulb upon vaporization of the absorbed fragrant oil therein;
repeating steps (b) and (c); and
thereafter replacing the porous ceramic ring with the fragrant oil again absorbed therein upon upper portions of the light bulb so as to again be removably supported thereon, whereby upon the light bulb again being energized, the absorbed fragrant oil in the porous ceramic ring will again be vaporized due to the heat applied thereto by the light bulb.

* * * * *